US012648874B2

(12) United States Patent
Grüebler et al.

(10) Patent No.: US 12,648,874 B2
(45) Date of Patent: Jun. 9, 2026

(54) GRASPING STRUCTURE FOR MEMBRANE REMOVAL

(71) Applicant: Alcon Inc., Fribourg (CH)

(72) Inventors: Reto Grüebler, Greifensee (CH); Luca Palmerini, Basel (CH)

(73) Assignee: Alcon Inc., Fribourg (CH)

( * ) Notice: Subject to any disclaimer, the term of this patent is extended or adjusted under 35 U.S.C. 154(b) by 99 days.

(21) Appl. No.: 18/430,839

(22) Filed: Feb. 2, 2024

(65) Prior Publication Data

US 2024/0268997 A1     Aug. 15, 2024

Related U.S. Application Data

(60) Provisional application No. 63/484,233, filed on Feb. 10, 2023.

(51) Int. Cl.
A61F 9/007     (2006.01)
A61B 17/30     (2006.01)
A61B 17/32     (2006.01)

(52) U.S. Cl.
CPC .... A61F 9/00754 (2013.01); A61B 2017/306 (2013.01); A61B 2017/320064 (2013.01)

(58) Field of Classification Search
CPC ............ A61F 9/00754; A61F 9/00736; A61B 2017/306; A61B 2017/320064
See application file for complete search history.

(56) References Cited

U.S. PATENT DOCUMENTS

| | | | | |
|---|---|---|---|---|
| 6,090,041 | A | * | 7/2000 | Clark ................. A61B 17/0218 |
| | | | | 600/206 |
| 6,800,076 | B2 | * | 10/2004 | Humayun ............... A61M 1/84 |
| | | | | 606/4 |
| 6,908,476 | B2 | | 6/2005 | Jud |
| 6,945,984 | B2 | | 9/2005 | Arumi |
| 9,320,534 | B2 | | 4/2016 | Vezzu |
| 9,827,141 | B2 | | 11/2017 | Schaller |
| 10,500,090 | B2 | | 12/2019 | Gunn et al. |
| 10,729,504 | B2 | | 8/2020 | Schaller |
| 10,973,682 | B2 | * | 4/2021 | Vezzu .................... A61B 17/30 |
| 11,224,539 | B2 | | 1/2022 | Grueebler |
| 11,490,915 | B2 | | 11/2022 | Abt |
| 11,751,909 | B2 | | 9/2023 | Schaller et al. |
| 11,759,237 | B2 | | 9/2023 | Schaller |
| 2014/0135820 | A1 | | 5/2014 | Schaller et al. |
| 2016/0296246 | A1 | | 10/2016 | Schaller |

(Continued)

OTHER PUBLICATIONS

Alcon Surgical Retina Product Catalog, 2019 (36 pages).

*Primary Examiner* — Brooke Labranche
(74) *Attorney, Agent, or Firm* — Patterson + Sheridan, LLP

(57)     ABSTRACT
An ophthalmic surgical instrument for delaminating a retinal membrane includes a handpiece and an actuator mounted on the handpiece. An outer tube has a proximal end mounted to the handpiece. A grasping structure is extendable outwardly relative to a distal end of the outer tube responsive to movement of the actuator. The grasping structure includes a cavity having an opening facing the retinal membrane in use. A blade extends along a portion of the opening and a cushion defining a plurality of openings is positioned within the cavity. Vacuum pressure is applied to a channel in the cushion and coupled to the openings in order to grasp the retinal membrane, which may then be peeled from the retina.

11 Claims, 6 Drawing Sheets

(56) References Cited

U.S. PATENT DOCUMENTS

| | | |
|---|---|---|
| 2021/0069017 A1 | 3/2021 | Awh |
| 2022/0117779 A1 | 4/2022 | Hallen |
| 2022/0296415 A1 | 9/2022 | Hassan |
| 2022/0346876 A1 | 11/2022 | Pollack |
| 2022/0362057 A1 | 11/2022 | Charles |

* cited by examiner

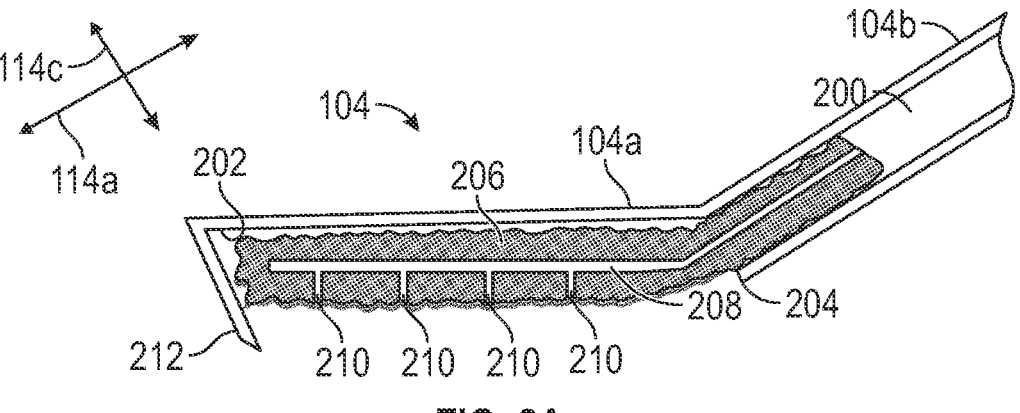
FIG. 2A
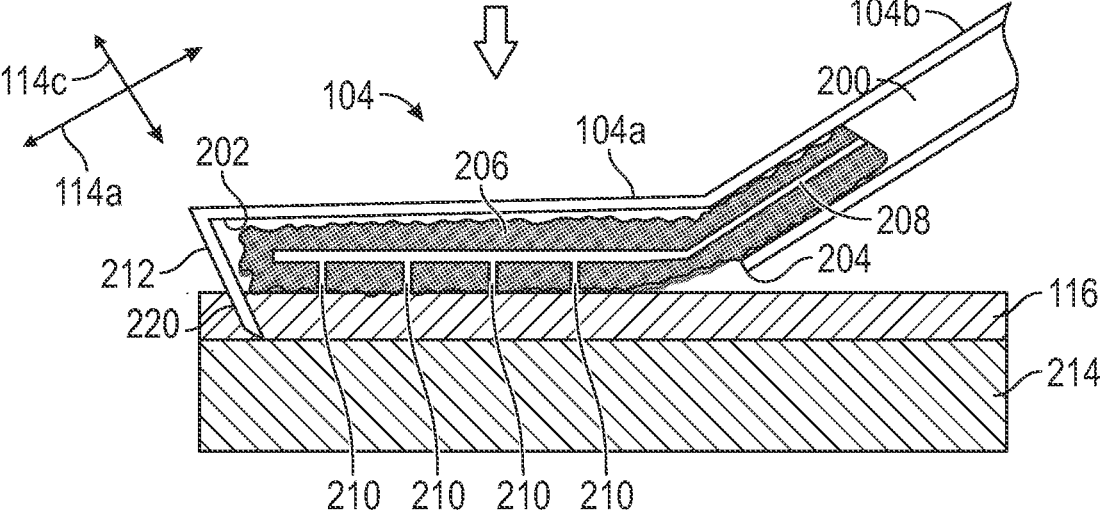
FIG. 2B
FIG. 2C

GRASPING STRUCTURE FOR MEMBRANE REMOVAL

BACKGROUND

The internal limiting membrane (ILM) is a thin transparent membrane positioned between the vitreous and the retina of the eye. The ILM plays a role during the formation of the eye but is not required for the proper function of an adult eye. The ILM may pull at the retina and cause conditions such as macular holes, macular pucker, vitreo-macular traction syndrome, diabetic macular edema, and cystoid macular edema secondary to inflammation or venous occlusive diseases and other conditions. An epiretinal membrane (ERM) is a membrane that may form over the retina in response to damage to the retina, such as due to posterior vitreous detachment.

The ILM or ERM may need to be peeled away from the retina to prevent damage to the retina. Peeling of the ILM or ERM may also be required in preparation for surgical procedures performed on the retina. To peel the ILM or ERM, a surgical instrument is inserted through a cannula within the patient's eye globe. Forceps or a specialized scraper are extended from the instrument and used to raise a flap in the ILM or ERM. The flap is then grasped by the forceps and the ILM or ERM is peeled away from the retina using a circular motion. However, excess force on the forceps may result in piercing of the retina.

It would therefore be an advancement in the art to reduce the risk of retinal damage resulting from membrane peeling.

BRIEF SUMMARY

The present disclosure relates generally to a grasping structure for peeling a retinal membrane.

Certain aspects provide an ophthalmic surgical instrument for peeling a retinal membrane. The ophthalmic surgical instrument includes a handpiece and an actuator mounted on the handpiece. An outer tube has a proximal end mounted to the handpiece. A grasping structure is extendable outwardly relative to a distal end of the outer tube responsive to movement of the actuator. The grasping structure defines a plurality of openings configured to be placed in fluid communication with a source of vacuum pressure.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

FIGS. 2A to 2C are cross-sectional views showing peeling of a retinal membrane with the vacuum activated grasping structure of FIG. 1, in accordance with certain embodiments.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure provide a surgical instrument for delaminating a membrane from a patient's retina. Note that, herein, a distal end of a component refers to the end that is closer to a patient's body while the proximal end of the component refers to the end that is facing away from the patient's body or in proximity to, for example, the handpiece of the surgical instrument.

Figure 1:
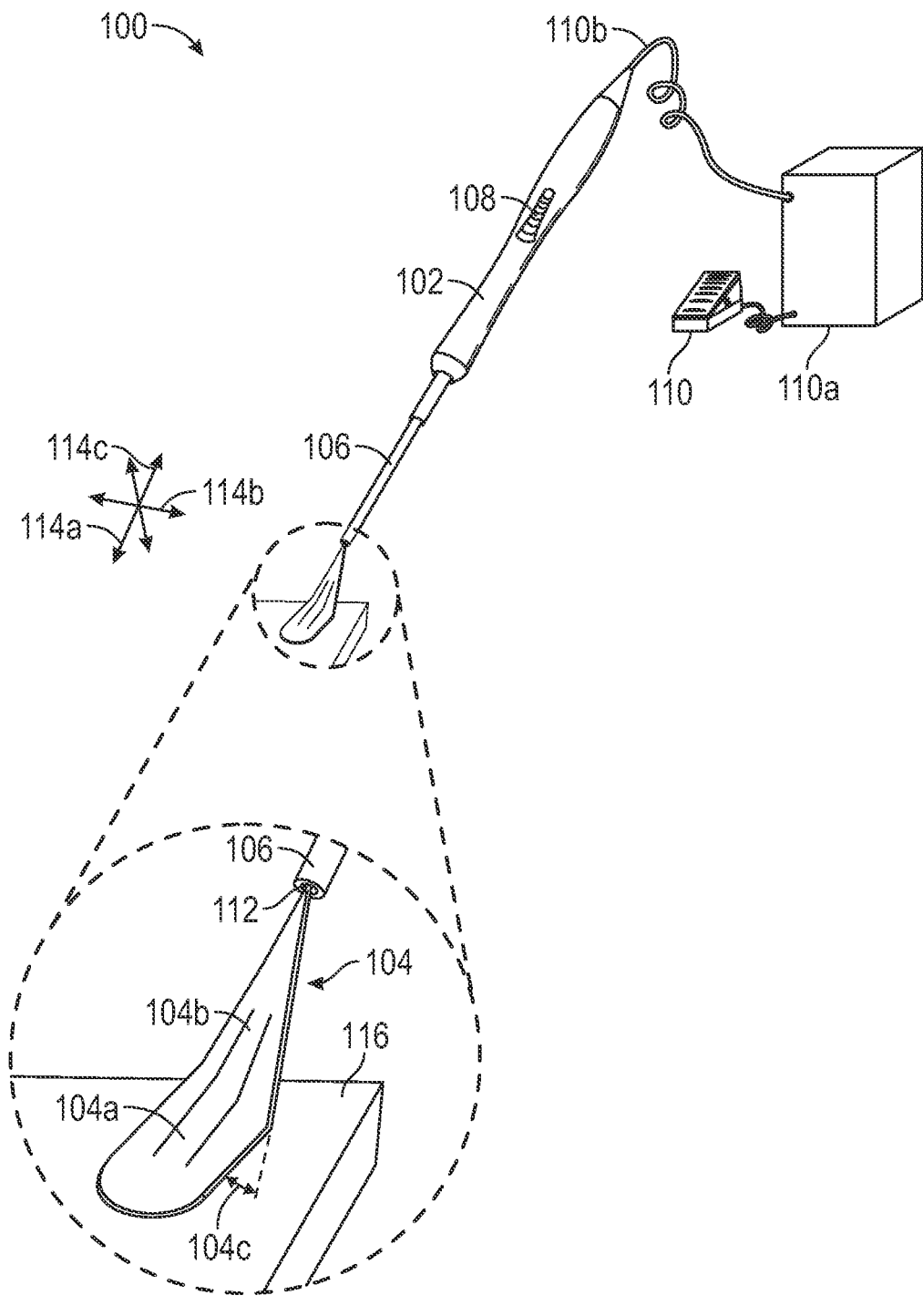
FIG. 1 is an isometric view of a surgical instrument having a vacuum activated grasping structure, in accordance with certain embodiments.

FIG. 1 illustrates a surgical instrument 100, in accordance with certain embodiments, including a handpiece 102 that is sized and contoured to be grasped by a hand of a surgeon performing an ophthalmic surgical procedure such as peeling of a membrane from a retina of a patient's eye, such as an ILM or ERM.

A grasping structure 104 is extendable relative to a distal end of an outer tube 106 connected to the handpiece 102. As discussed in greater detail below, the grasping structure 104 is vacuum activated. The proximal end of the outer tube 106 is connected to the handpiece 102. The handpiece 102 may have one or more manual control structures mounted thereto. In the embodiments of FIG. 1, the manual control structures include a slider 108. The slider 108 may be used to control extension of the grasping structure 104 relative to the outer tube 106, and may, in certain embodiments, be replaced with a deformable basket. Vacuum supplied to the grasping structure 104 may additionally be controlled by means of a foot pedal 110 controlling air flow to the grasping structure 104, such as the supply of vacuum pressure from a vacuum generator 110a through a flexible tube 110b coupling the vacuum generator 110a to the handpiece 102. In other implementations, the flow of air may be controlled by a button mounted to the handpiece 102. Vacuum generator 110a may be implemented as part of a surgical console.

The grasping structure 104 may be connected to a hollow rod 112 extending through the outer tube 106. In a first implementation, the hollow rod 112 is fixed relative to the handpiece 102 whereas the outer tube 106 is slidable relative to the handpiece 102 and is coupled to the slider 108 to be actuated thereby. In a second implementation, the hollow rod 112 is coupled to the slider 108 and is actuated thereby, whereas the outer tube 106 is fixed relative to the handpiece 102.

A longitudinal direction 114a may be defined as parallel to the axis of symmetry of the outer tube 106. A transverse direction 114b may be defined as perpendicular to the longitudinal direction 114a and a vertical direction 114c may be defined as perpendicular to the longitudinal direction 114*a* and the transverse direction 114*b*.

The grasping structure 104 extends distally from the hollow rod 112 and increases in width in the transverse direction 114*b* such that the grasping structure 104, at its widest point in the transverse direction 114*b*, is many times greater than the thickness of the grasping structure 104 perpendicular to the transverse direction 114*b*, such as greater than 5, 10, 20, or 30 times the thickness. The width of the grasping structure 104 at its widest point may also be greater than the inner diameter of the outer tube 106, such as greater than 1.1 or greater than 2 times the inner diameter. Accordingly, when retracted within the outer tube 106, the grasping structure 104 may curl or bend in order to fit within the outer tube 106. The grasping structure 104 and hollow rod 112 may be made of a flexible material such as nitinol, spring steel, or a flexible polymer.

The grasping structure 104 may be bent or curved in one or more section planes. For example, the grasping structure 104 may be bent or curved in a plane parallel to the longitudinal direction 114*a* and the vertical direction 114*c* ("the longitudinal-vertical plane"). The bend or curvature of the grasping structure 104 provides a distal portion 104*a* that is angled with respect to the longitudinal direction 114*a* and is closer to parallel with respect to the retinal membrane 116 that is grasped using the grasping structure 104. Flexibility of the grasping structure 104 may enable deformation of the grasping structure 104 such that the distal portion 104*a* lies flat on the retinal membrane 116. In practice, the grasping structure 104 is inserted through a trocar cannula that is to one side of the pupil of the patient's eye, whereas the retinal membrane 116 to be peeled is located behind the pupil. Accordingly, the longitudinal direction 114*a* will be non-parallel to the normal of the retinal membrane 116 at a point of contact with the grasping structure 104. An angle 104*c* defined by the distal portion 104*a* with respect to the longitudinal direction 114*a* in the longitudinal-vertical plane may account for this non-normal angle. For example, the angle 104*c* may be an angle between 85 and 45, 80 and 50, or 75 and 55 degrees.

The distal portion 104*a* may be connected to the hollow rod 112 by a proximal portion 104*b* that may flare outwardly from the width of the hollow rod 112 to a width of the distal portion 104*a* in the transverse direction 114*b*. The distal portion 104*a* may be parallel to the longitudinal direction 114*a* other than a curved transition to the angled orientation of the distal portion 104*a*.

FIGS. 2A to 2C illustrate the grasping structure 104 during use as well as the internal structure of the grasping structure 104. Proximal portion 104*b* may define a channel 200 in fluid communication with the hollow rod 112 such that vacuum pressure supplied to the hollow rod 112 from the vacuum generator 110*a* is transmitted through the channel 200. The grasping structure 104 may define a cavity 202 that is in fluid communication with the channel 200 and is accessible through an opening 204. The opening 204 may extend across substantially all (e.g., at least 90 percent) of an underside (side facing the retinal membrane 116) of the distal portion 104*a* and may extend partially along the proximal portion 104*b*. The cavity 202 may be occupied by a cushion 206 made of a flexible material, such as silicone. The cushion 206 defines one or more channels 208 that are in fluid communication with channel 200. The cushion 206 may extend into the channel 200 and may provide a seal that hinders fluid flow into the channel 200 other than through the one or more channels 208. The one or more channels 208 connect to an array of openings 210 on the underside (surface facing outwardly through the opening 204) of the cushion 206. The openings 210 are shown distributed in one dimension but may be distributed in a two-dimensional array (ordered or random) across the underside of the cushion 206.

A blade 212 may extend across a distal end of the opening 204. The blade 212 extends downwardly past the underside of the cushion 206 by a distance that is slightly less than the thickness of the retinal membrane 116, which is typically about 4 microns. In the illustrated embodiment, the blade 212 secures to a distal end of the distal portion 104*a* and defines an edge of the opening 204 that is opposite the proximal portion 104*b*. When the cushion 206 is pressed against the retinal membrane 116, the blade 212 may extend downwardly into the membrane by between 0.6 and 0.9 times the thickness of the retinal membrane 116, e.g., between 1 and 3.6 microns, such as between 2.4 and 3.6 microns.

Referring to FIG. 2B, in use, the outer tube 106 is inserted through a trocar cannula and the grasping structure 104 is extended relative to the outer tube 106 by either withdrawing the outer tube 106 or pushing the grasping structure 104 out of the outer tube 106. The cushion 206 is pressed against the retinal membrane 116 and the blade 212 is pressed into the retinal membrane 116, thereby creating an incision 220 in the retinal membrane 116. Vacuum pressure is supplied through the hollow rod 112 and channel 200 to the one or more channels 208, thereby inducing a vacuum at the openings 210.

Referring to FIG. 2C, the vacuum pressure at the openings 210 adheres a portion 116*a* of the cushion 206 and distal portion 104*a* to the retinal membrane 116. The grasping structure 104 may then be lifted away from the retina 214 thereby separating the portion 116*a* of the retinal membrane 116 from the retina 214.

Figure 3:
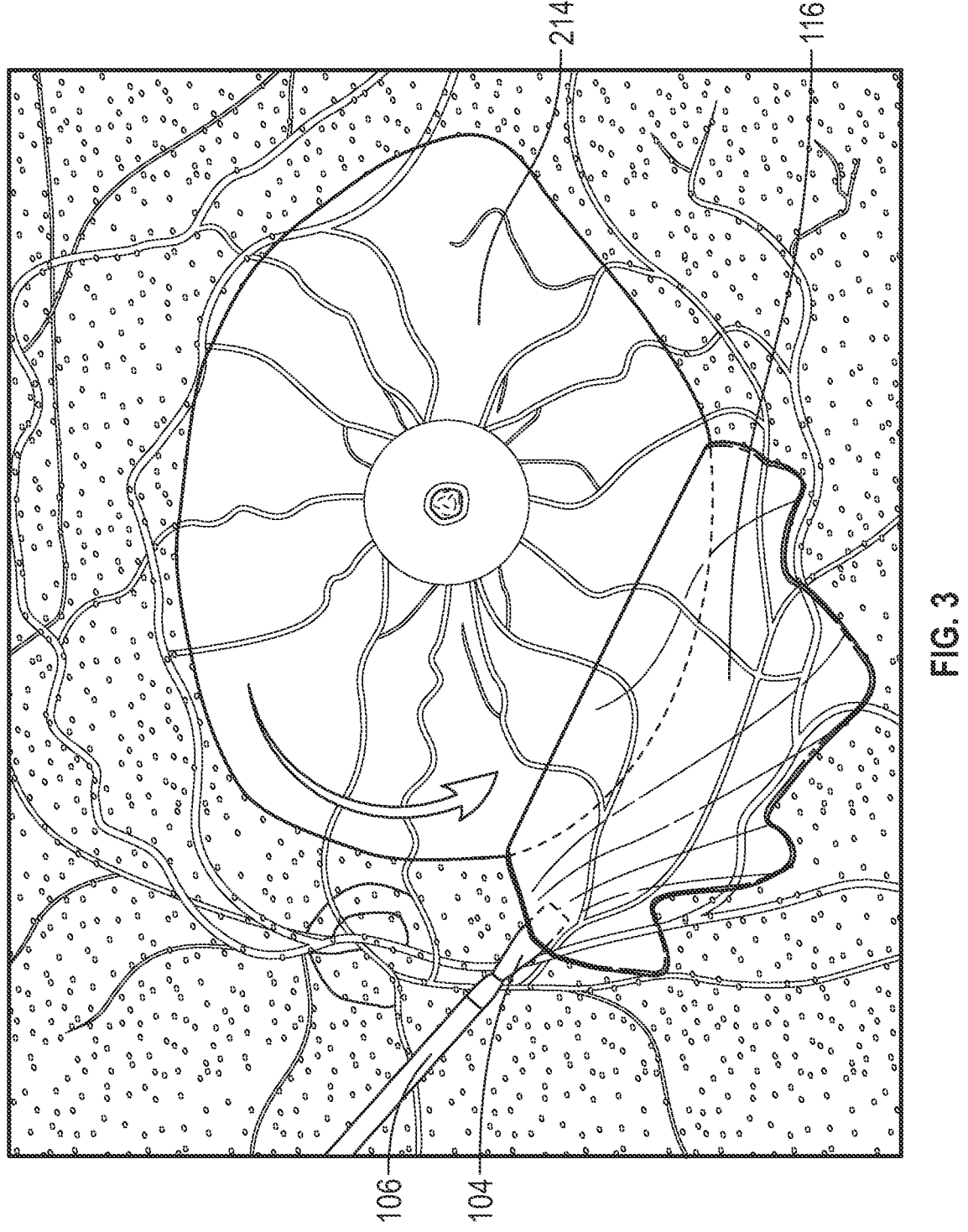
FIG. 3 is an isometric view showing an ILM being peeled using the vacuum activated grasping structure of FIG. 1, in accordance with certain embodiments.

Referring to FIG. 3, the grasping structure 104 may then be moved in a circular motion to remove the separated portion of the retinal membrane 116 from the retina. The grasping structure 104 may then be withdrawn into the outer tube 106 and grasping structure 104 and outer tube 106 may be withdrawn through the trocar cannula. Vacuum pressure may continue to be supplied to the openings 210 as the grasping structure 104 is withdrawn such that the peeled portion of the membrane 116 is also withdrawn through the trocar cannula.

Figure 4A:
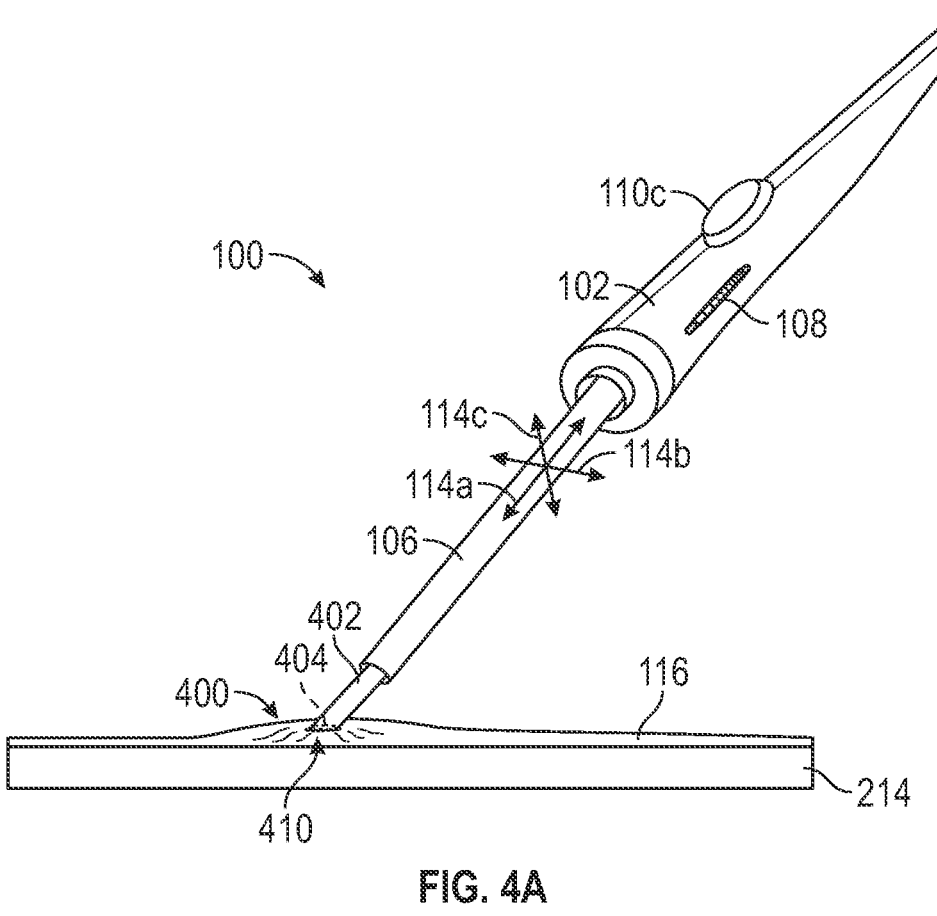
FIG. 4A is an isometric view of an alternative embodiment of a vacuum activated grasping structure, in accordance with certain embodiments.
Figure 4B:
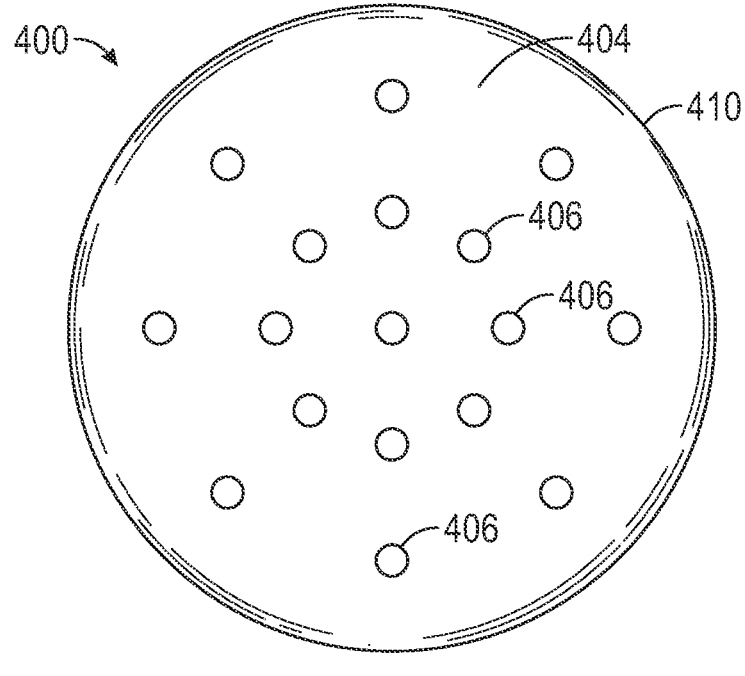
FIG. 4B is a bottom view of the vacuum activated grasping structure of FIG. 4A, in accordance with certain embodiments.

FIGS. 4A and 4B illustrate an alternative implementation of the surgical instrument 100 for peeling of a membrane from a retina of a patient's eye, such as an ILM or ERM, in accordance with certain embodiments.

As shown, a vacuum activated grasping structure 400 includes a tube 402 that is extendable relative to the outer tube 106 by actuation of the slider 108 or alternative manual control structure. Similar to the previous embodiment, the outer tube 106 may be actuated by the slider 108 and the tube 402 may be fixed relative to the handpiece 102, or the tube 402 may be actuated by the slider 108 and the outer tube 106 may be fixed relative to the handpiece 102. In the embodiment of FIG. 4A, supply of vacuum pressure to the tube 402 is controlled by a button 110*c* on the handpiece 102. The button 110*c* may control supply of power to the vacuum generator 110*a* or may actuate a valve coupling vacuum pressure to the tube 402 when the button 110*c* is pressed or otherwise actuated. The button 110*c* may also be used in place of the foot pedal 110 in the embodiment of FIGS. 1 to 2C.

A distal end of the tube 402 may include a distal endface 410 having a perforated cover 404 with a plurality of openings 406 (shown in FIG. 4B). The perforated cover 404 may be made of the same material as the tube 402, e.g., nitinol. Alternatively, the tube 402 may be made of nitinol whereas the cover 404 is made of a flexible material, such as silicone or other polymer.

The distal endface 410 of the tube 402 may be at an angle relative to the longitudinal direction 114*a*. For example, as shown in FIG. 4A, the distal endface 410 of the tube 402 may be at an angle in the longitudinal-vertical plane. For example, the angle may be between 85 and 45, 80 and 50, or 75 and 55 degrees. The angle may facilitate placing of the distal endface 410 of the tube 402 and the cover 404 flat against the membrane 116.

In use, the outer tube 106 may be inserted through a trocar cannula, the tube 402 extended relative to the outer tube 106, the cover 404 placed against the membrane 116, and the button 110*c* actuated to supply vacuum pressure through the tube 402 to the openings 406. The membrane 116 will then be drawn against the cover 404. The surgeon may then pull on the handpiece 102 in order to detach the membrane 116 from the retina 214. The surgeon may move the grasping structure 400 in a circular motion as shown in FIG. 3 in order to remove a portion of the membrane 116. The grasping structure 400 may then be withdrawn into the outer tube 106 and grasping structure 104 and outer tube 106 may be withdrawn through the trocar cannula. Vacuum pressure may continue to be supplied to the openings 406 as the grasping structure 104 is withdrawn such that the peeled portion of the membrane 116 is also withdrawn through the trocar cannula.

Figure 4C:
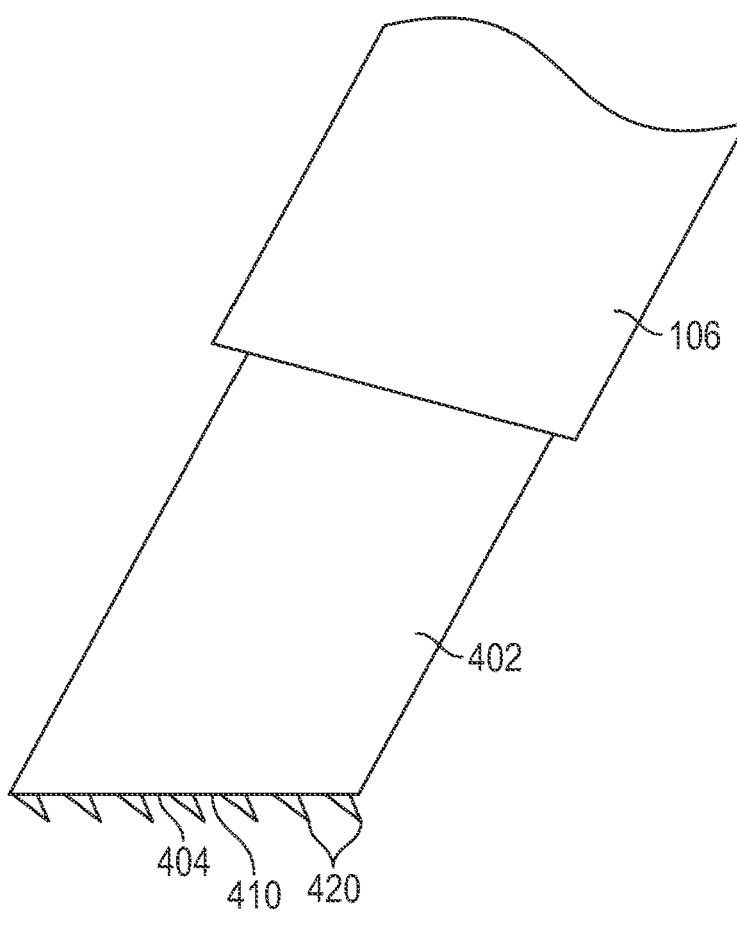
FIG. 4C is an isometric view of another alternative embodiment of a vacuum activated grasping structure, in accordance with certain embodiments.
Figure 4D:
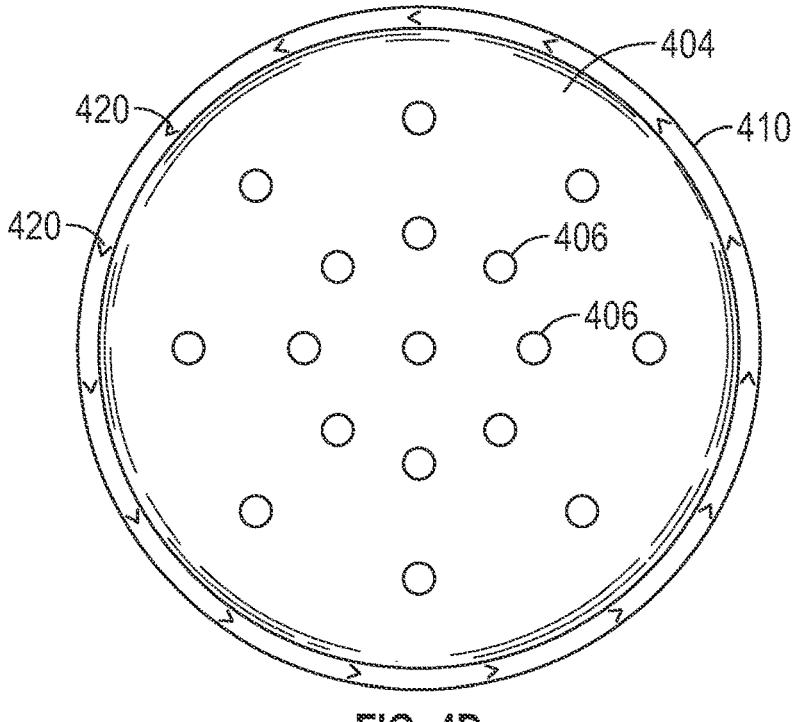
FIG. 4D is a view of a distal endface of a vacuum activated grasping structure, in accordance with certain embodiments.

Turning now to FIGS. 4C and 4D, in some embodiments, teeth 420 may be provided on at least a portion of the distal endface 410 in order to cut the membrane 116. For example, the teeth 420 may be disposed circumferentially around at least a portion (e.g., a 180 to 90 degree sector) of the cover 404 and/or openings 406. The teeth 420 may have a height of between about 2 microns and about 20 microns from the surface of the distal endface 410, such as a height of between about 5 microns and about 15 microns from the surface of the distal endface 410, such as a height of about 10 microns from the surface of the distal endface 410. In certain embodiments, the teeth 420 may be angled at an angle between about 30 degrees and about 90 degrees relative to the longitudinal direction 114*a*, such as an angle between about 45 degrees and about 75 degrees relative to the longitudinal direction 114*a*.

Figure 4E:
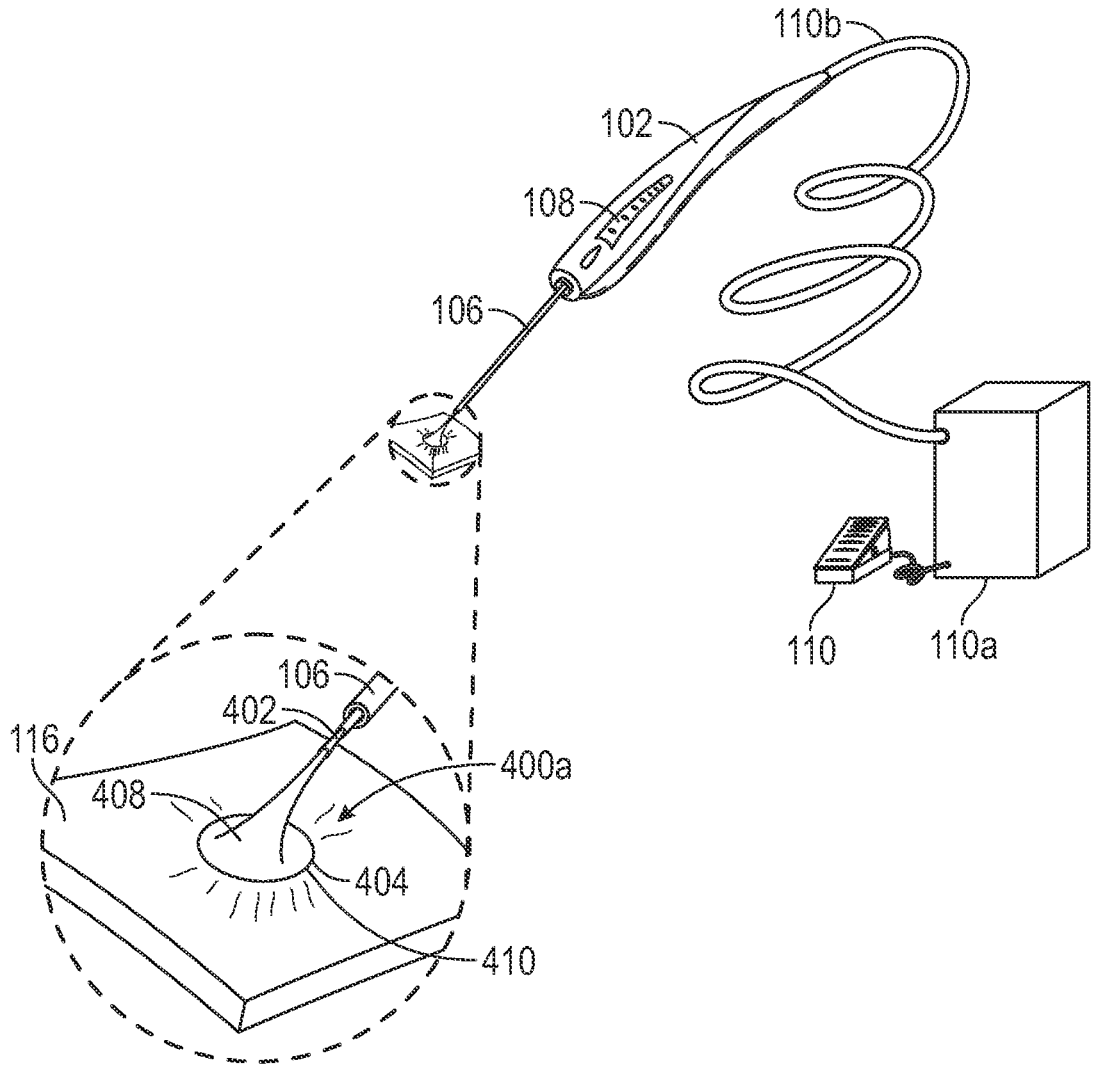
FIG. 4E is a view of a vacuum activated grasping structure engaging a membrane, in accordance with certain embodiments.

Referring to FIG. 4E, the grasping structure 400 of the embodiments of FIGS. 4A-4D may be modified as illustrated to achieve the illustrated grasping structure 400*a*. The grasping structure 400*a* may be used in the same manner as the grasping structure 400 of FIGS. 4A-4D. In the grasping structure 400*a*, a distal portion 408 secured to, or formed by part of, the tube 402 may be flared, such as a trumpet or conical shape. In such embodiments, the diameter of the distal endface 410 of the distal portion 408 may be greater than the inner diameter of the outer tube 106 such that folding or other deformation of the distal portion 408 is required for the distal portion 408 to enter the outer tube 106. The distal portion 408 may be made of a different material than the tube 402. For example, the distal portion 408 may be made of silicone or other elastomer whereas the remainder of the tube 402 is made of nitinol. A cover 404 having openings 406 may extend over at least a portion of the distal endface 410 of distal portion 408, such as shown in the embodiments of FIG. 4B. Where the distal portion 408 is made of the same material as the cover 404, the distal portion and cover 404 may be monolithically formed such as by co-molding. Teeth may be provided around a portion of the perimeter of the distal end of the tube 402, such as shown in the embodiments of FIGS. 4C-4D. Flexibility of the distal portion 408 may enable the distal portion 408 to compensate for a difference in orientation of the cover 404 and the membrane 116 and to reduce the amount of force transmitted from the handpiece 102 to the membrane 116. In the embodiment of FIG. 4E, a foot pedal 110 is used to control supply of vacuum pressure to the tube 402. However, a button 110*c* may also be used as shown in the embodiments of FIG. 4A.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. An ophthalmic surgical instrument for peeling a retinal membrane, comprising:
   a handpiece;
   an actuator mounted on the handpiece;
   an outer tube having a proximal end mounted to the handpiece; and
   a grasping structure extendable outwardly relative to a distal end of the outer tube responsive to movement of the actuator, the grasping structure defining a cavity having an opening configured to face the retinal membrane, the grasping structure comprising:
      a cushion positioned within the cavity, the cushion comprising an underside facing outwardly from the cavity, the cushion defining:
         a channel configured to be placed in fluid communication with a source of vacuum pressure; and
         a plurality of openings on the underside, the plurality of openings in fluid communication with the channel; and
      a blade extending across a distal end of the opening and downwardly past the underside of the cushion.

2. The ophthalmic surgical instrument of claim 1, wherein the blade extends outwardly from the opening by between 1 and 3.6 microns.

3. The ophthalmic surgical instrument of claim 1, wherein the cushion extends from the cavity into a proximal portion of the grasping structure.

4. The ophthalmic surgical instrument of claim 1, wherein the cushion comprises silicone.

5. The ophthalmic surgical instrument of claim 1, further comprising a hollow tube connecting the grasping structure to the handpiece, the hollow tube in fluid communication with the channel and configured to be placed in fluid communication with the source of vacuum pressure.

6. The ophthalmic surgical instrument of claim 5, wherein the grasping structure includes a proximal portion secured to the hollow tube and a distal portion secured to the proximal portion and being angled with respect to the proximal portion, the distal portion defining the cavity and having the blade secured thereto.

7. The ophthalmic surgical instrument of claim 1, further comprising a button mounted to the handpiece and configured to control supply of vacuum pressure to the grasping structure from the source of vacuum pressure.

8. The ophthalmic surgical instrument of claim 1, further comprising a foot pedal coupled to the source of vacuum pressure and the grasping structure, the foot pedal configured to control supply of vacuum pressure to the grasping structure from the source of vacuum pressure.

9. A method for peeling a membrane from a retina, the method comprising:

pressing a grasping structure of an ophthalmic surgical instrument against the membrane, the ophthalmic surgical instrument further comprising:

a handpiece;

an actuator mounted on the handpiece; and an outer tube having a proximal end mounted to the handpiece;

wherein:

the grasping structure is extendable outwardly relative to a distal end of the outer tube responsive to movement of the actuator, the grasping structure defines a cavity having an opening configured to face the membrane, the grasping structure comprises a cushion positioned within the cavity, the cushion comprising an underside facing outwardly from the cavity, the cushion defining a channel configured to be placed in fluid communication with a source of vacuum pressure, the underside defining a plurality of openings in fluid communication with the channel, and the grasping structure further comprises a blade extending across a distal end of the opening and downwardly past the underside of the cushion; and supplying vacuum pressure to the plurality of openings.

10. The method of claim 9, further comprising removing a portion of the membrane from the retina by pulling the grasping structure away from the retina.

11. The method of claim 9, wherein the blade is configured to cut the membrane when the underside of the grasping structure is pressed against the membrane.

\* \* \* \* \*